(12) United States Patent
Lehmann et al.

(10) Patent No.: US 9,504,463 B2
(45) Date of Patent: *Nov. 29, 2016

(54) DEVICE FOR ANCHORING A SUTURE IN TISSUE

(71) Applicant: Woodwelding AG, Stansstad (CH)

(72) Inventors: Mario Lehmann, Les Pommerates (CH); Laurent Torriani, Lamboing (CH); Stephanie Mehl, Zug (CH); Jörg Mayer, Niederlenz (CH)

(73) Assignee: WOODWELDING AG, Stansstad (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/852,782

(22) Filed: Sep. 14, 2015

(65) Prior Publication Data

US 2015/0374357 A1     Dec. 31, 2015

Related U.S. Application Data

(60) Continuation of application No. 14/107,248, filed on Dec. 16, 2013, now Pat. No. 9,149,269, which is a division of application No. 12/920,696, filed as application No. PCT/CH2009/000082 on Mar. 2, 2009, now Pat. No. 8,623,050.

(60) Provisional application No. 61/033,066, filed on Mar. 3, 2008.

(51) Int. Cl.
*A61B 17/04*       (2006.01)
*A61B 17/00*       (2006.01)
*A61F 2/30*         (2006.01)

(52) U.S. Cl.
CPC .. *A61B 17/0401* (2013.01); *A61B 2017/00955* (2013.01); *A61B 2017/042* (2013.01);

(Continued)

(58) Field of Classification Search
CPC .............. A61B 17/0401; A61B 2017/0414; A61B 2017/042; A61B 2017/0458; A61B 2017/00955; A61B 2017/0409; A61B 2017/0446; A61B 2017/0448; A61B 2017/0451; A61B 2017/045; A61F 2002/30065; A61F 2210/0071
See application file for complete search history.

(56) References Cited

U.S. PATENT DOCUMENTS

| 5,545,180 A | 8/1996 | Le et al. |
|---|---|---|
| 6,287,325 B1 | 9/2001 | Bonutti |

(Continued)

FOREIGN PATENT DOCUMENTS

| EP | 2537470 | 12/2012 |
|---|---|---|
| JP | 8-173436 | 7/1996 |

(Continued)

*Primary Examiner* — Alexander Orkin
(74) *Attorney, Agent, or Firm* — Rankin, Hill & Clark LLP

(57) ABSTRACT

A device for the anchoring of a suture in tissue includes a guide sleeve, a sonotrode, an anchor and the suture. The guide sleeve has a distal part with a smaller cross section and a proximal part with a larger cross section. The sonotrode extends through the lumen of the guide sleeve and has a distal end and a proximal end, the proximal end being designed for coupling the sonotrode to a vibration source (e.g. an ultrasonic device). The anchor is arranged at the distal end of the device and includes an anchor foot and an anchoring sleeve sitting on a shoulder of the anchor foot. The anchoring sleeve consists of a material which is liquefiable through mechanical vibrations. A middle portion of the suture runs through the anchor foot and two end portions of the suture are attached to the guide sleeve.

20 Claims, 6 Drawing Sheets

(52) U.S. Cl.
CPC  *A61B2017/0409* (2013.01); *A61B 2017/0412* (2013.01); *A61B 2017/0414* (2013.01); *A61B 2017/0417* (2013.01); *A61B 2017/0422* (2013.01); *A61B 2017/0445* (2013.01); *A61F 2002/30065* (2013.01); *A61F 2210/0071* (2013.01)

(56) References Cited

U.S. PATENT DOCUMENTS

| | | |
|---|---|---|
| 6,610,079 B1 | 8/2003 | Li et al. |
| 8,403,938 B2 | 3/2013 | Aeschlimann et al. |
| 8,623,050 B2 | 1/2014 | Lehmann et al. |
| 9,149,269 B2 * | 10/2015 | Lehmann et al. |
| 2003/0083662 A1 | 5/2003 | Middleton |
| 2004/0030341 A1 | 2/2004 | Aeschlimann et al. |
| 2004/0044366 A1 | 3/2004 | Bonutti et al. |
| 2004/0138706 A1 * | 7/2004 | Abrams et al. ............. 606/232 |
| 2005/0222575 A1 | 10/2005 | Ciccone et al. |
| 2006/0074422 A1 | 4/2006 | Story et al. |
| 2007/0093858 A1 | 4/2007 | Gambale et al. |
| 2007/0265704 A1 | 11/2007 | Mayer et al. |
| 2007/0270974 A1 | 11/2007 | Aeschlimann et al. |
| 2009/0024161 A1 | 1/2009 | Bonutti et al. |
| 2009/0131947 A1 | 5/2009 | Aeschlimann et al. |
| 2012/0179200 A1 | 7/2012 | Cauldwell et al. |
| 2012/0245634 A1 | 9/2012 | Kaplan |
| 2012/0330327 A1 | 12/2012 | McClellan |
| 2013/0023930 A1 | 1/2013 | Stone et al. |
| 2013/0046340 A1 | 2/2013 | Huxel et al. |
| 2013/0072976 A1 | 3/2013 | Van Der Burg et al. |
| 2013/0123848 A1 | 5/2013 | Duggal et al. |
| 2013/0138123 A1 | 5/2013 | Stone et al. |
| 2013/0138152 A1 | 5/2013 | Stone et al. |
| 2013/0150885 A1 | 6/2013 | Dreyfuss |

FOREIGN PATENT DOCUMENTS

| | | |
|---|---|---|
| JP | 10-503389 | 3/1998 |
| JP | 2004-500175 | 1/2004 |
| JP | 2006-095301 | 4/2006 |
| JP | 2007-271773 | 10/2007 |
| JP | 2011-500230 | 1/2011 |
| WO | 02069817 | 9/2002 |
| WO | 2004017857 | 3/2004 |
| WO | 2005079696 | 9/2005 |
| WO | 2009055952 | 5/2009 |
| WO | 2011/119684 | 9/2011 |

* cited by examiner

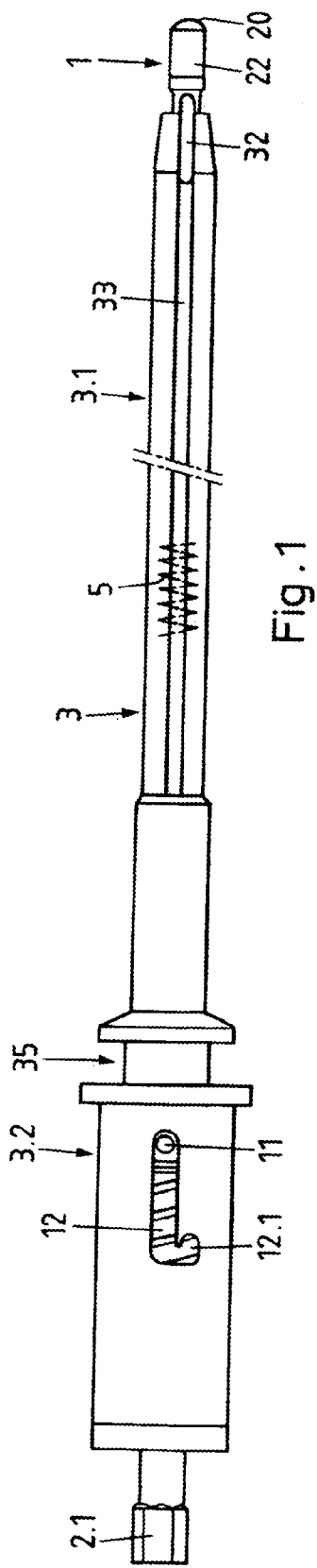
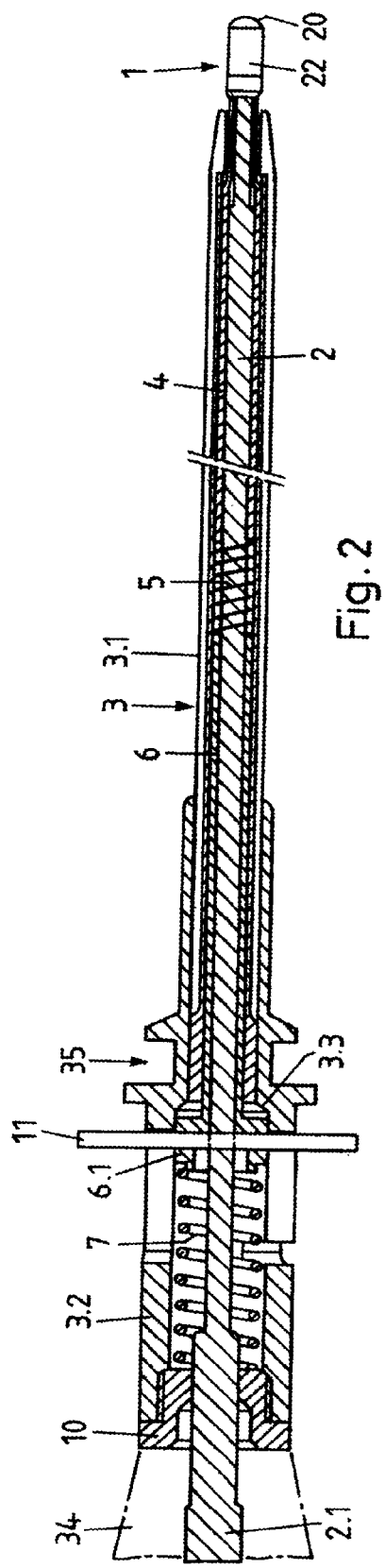

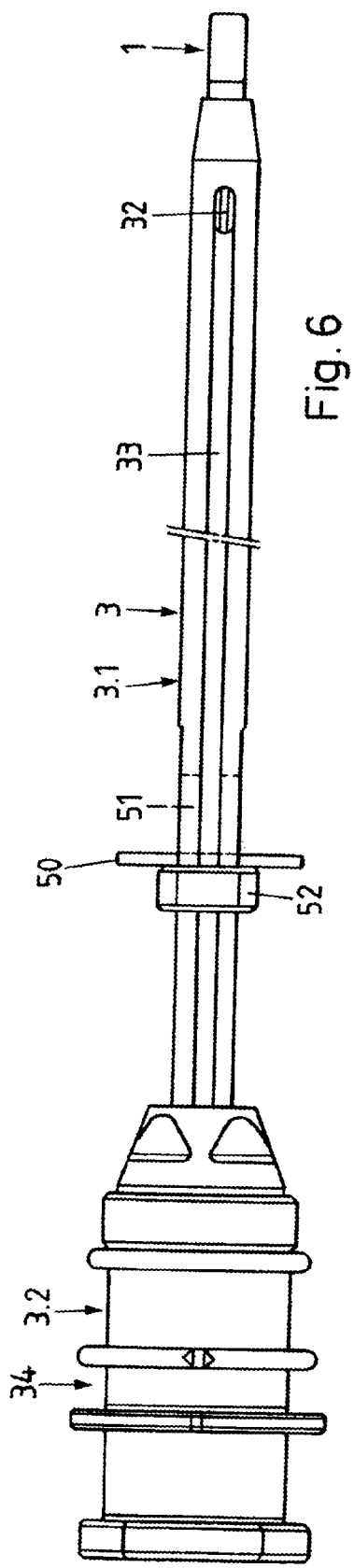
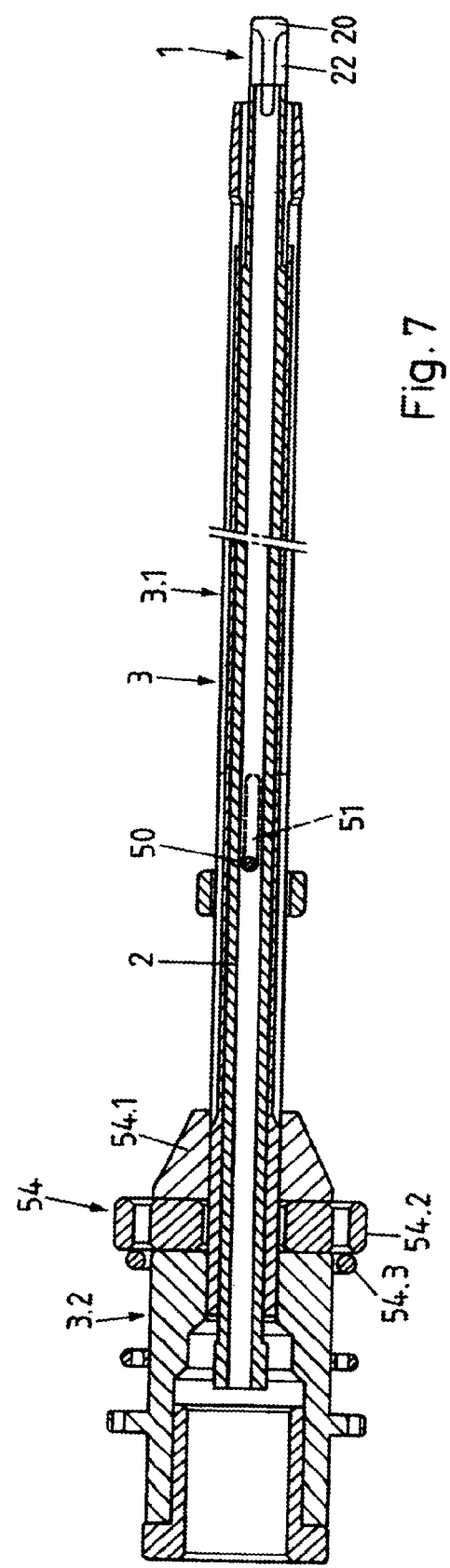

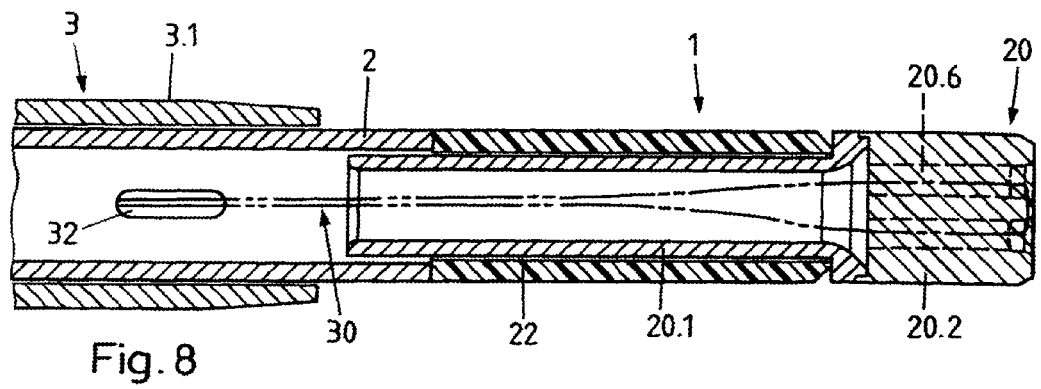
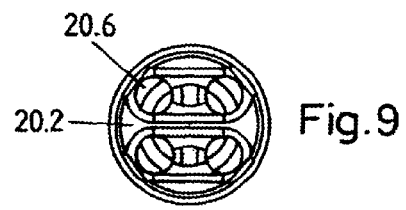
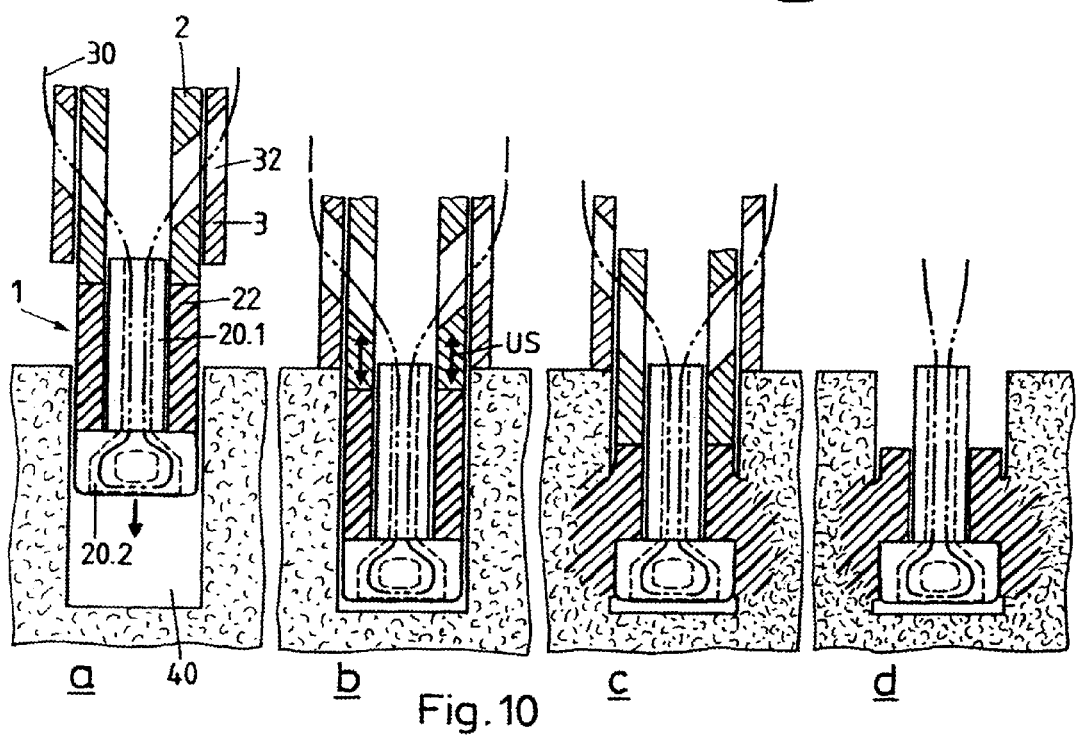

DEVICE FOR ANCHORING A SUTURE IN TISSUE

BACKGROUND OF THE INVENTION

Field of the Invention

The invention concerns the field of medical technology and pertains to a device for the anchoring of a suture in tissue, for instance in bone tissue.

Description of Related Art

The anchoring of sutures in human or animal bone tissue is used in techniques for medical and veterinary procedures, for instance for re-attaching of tendons and ligaments in the vicinity of joints. The bone in which this anchoring is undertaken has a dense outer layer (cortical bone), having a thickness on the order of 1 to 2 mm, and on the inside turning into of less dense bone tissue (spongiosa, or cancellous bone). Depending on the patient, the cancellous bone can have very different properties, in particular, depending on the age and health of the patient, this bone can have very different mechanical stability and regenerative ability.

According to the state of the art, various screw-shaped anchors are used for the anchoring of sutures in bone tissue. These screw-shaped anchors are inserted into bore reaching e.g. through the cortical bone and, if the cancellous bone has only little mechanical stability, their hold in the bone tissue relies primarily on the cortical bone. Radially compressible anchors are also used for the anchoring of sutures in bone tissue. These anchors are equipped with, for instance, deformable barbs and are inserted through the cortical bone into the cancellous bone, where the barbs expand and/or catch, depending on the mechanical resistance offered by the cancellous bone. These anchors are impacted into the bone tissue, for example, through bores provided at least through the cortical bone. A third known approach to anchoring sutures is to pre-drill an opening at least through the cortical bone, insert the anchor through the opening into the cancellous bone and, usually with the help of the suture, turn the anchor approximately 90 degrees. As the anchor is longer than wide, the turning brings the anchor into an orientation in which it can no longer be extracted through the pre-drilled opening and is therewith anchored in the cortical bone. The publications WO 02/069817, WO 04/017857 and WO 05/079696 disclose further anchoring procedures, which are suitable for the anchoring of sutures in tissue. The disclosed procedures rely on the liquefaction of a thermoplastic material via the application of mechanical vibrations, for instance ultrasonic vibrations, wherein for such liquefaction, friction between the bone tissue and the thermoplastic material and therewith a minimal mechanical strength of the tissue is needed.

The attachment of sutures to state of the art suture anchors is achieved, for example by the use of proximal eyelets, wherein anchors and eyelets are designed such that the implanted anchor does not protrude above the bone surface and the suture can pass freely through the eyelet after the implantation of the anchor. If a such anchored suture is to be used for the attachment of a tendon or ligament and is to cut into the bone tissue as little as possible, it is advantageous that the suture be attached to the anchor as near as possible to the bone surface. With respect to the suture anchors, it is also desirable that the strength of the anchorage corresponds to the strength of the eyelet and the suture. Anchor cross sections on the order of 5 mm or smaller are desirable, not only for application in minimally-invasive surgery, but also for allowing small pre-drilled bores in the bone tissue such that anchors can be implanted at small distances from each other. Furthermore, it is desirable for the surgeon to be able to place the anchor using only one hand.

The known suture anchors described above are usually designed for specific anchorage locations and also for specific bone qualities, not least because the known anchorage principles are not very widely applicable. This means that the surgeon must select one or another type of anchor for each operation, or even multiple types of anchors must be used for a single operation.

BRIEF SUMMARY OF THE INVENTION

The object of the invention is to create a device for the anchoring of sutures in tissue, for example in bone tissue, which device fulfills the needs and desires discussed above. Furthermore, the strength of the anchoring should be largely independent of the mechanical properties of the tissue or it should be adjustable on an ad-hoc basis to such properties.

This object is achieved by the device for the anchoring of a suture in tissue, as defined in the patent claims.

The device according to the invention, which device serves for the anchoring of a suture in tissue, is based on the anchoring method described in patent applications U.S. Ser. No. 12/260,698 and PCT/CH2008/000452. At the time of filing, the present application, the cited applications have not yet been published. The full contents of the cited patent applications are contained herein by reference.

The named anchoring method is based on the liquefaction of a material, that is liquefiable by mechanical vibrations between two anchor parts, the liquefaction being achieved by holding the two anchor parts against each other and by directly or indirectly connecting one of the anchor parts to a vibration source (for instance, an ultrasonic device) and impelling it to vibrate (for instance, impelled to ultrasonic vibration). At the same time, the two anchor parts are moved against one another, so that the liquefied material flows out from between the two anchor parts and penetrates into the surrounding tissue, where, on re-solidification it forms a positive connection between the anchor and the tissue and advantageously also between the two anchor parts.

For the anchoring process, the anchor parts are positioned in a tissue opening having a slightly larger cross-section than the anchor parts such that the anchor parts can be positioned without causing stress in the tissue. The only interaction with the tissue is the aforementioned penetration of the liquefied material, which is possible even in tissue with little mechanical strength, and which can even strengthen such tissue. The quantity of liquefied material can easily be selected for each particular anchoring process by simply pre-selecting a suitably long stroke of the two anchor elements relative to each other, or the surgeon can even decide on the length of the stroke during the anchoring process. For the aforementioned reasons the anchoring method, upon which the device according to the present invention is based, is not only suitable for bone tissues with various mechanical properties, but also for other tissues and it is therefore more generally applicable than other known anchoring methods.

The device according to the invention comprises an anchor with an opening (e.g. an eyelet) and a suture, wherein the suture is arranged such that it runs freely through the opening. The device further comprises a sonotrode (vibration transmitting element), and a guide sleeve, and, if applicable, further elements. The various elements of the device are arranged relative to one another in an essentially ready-to-use way.

The anchor forms the distal end of the device and comprises a distal anchor foot and an anchoring sleeve that sits on the anchor foot, wherein this anchoring sleeve comprises the material which is liquefiable by mechanical vibration (e.g. ultrasonic vibration). The sonotrode extends through the guide sleeve and reaches from the proximal end of the device to the proximal portion of the anchor. The sonotrode is designed for being able to transmit vibrations with as little loss of vibrational energy as possible from its proximal end to its distal end and the proximal sonotrode end is designed for being couplable to a vibration source. The anchoring sleeve is clamped between the anchor foot and the sonotrode, or a pushing sleeve, or the guide sleeve.

For the anchoring, the device is connected to the vibration source, its distal end, or the anchor respectively, is positioned in a tissue opening and the vibration source is activated. The liquefiable material of the clamped anchoring sleeve is liquefied by the vibration which acts on the anchoring sleeve either through direct contact between the anchoring sleeve and the sonotrode or indirectly via the anchor foot. At the same time, the anchoring sleeve is moved relative to the anchor foot with the aid of the sonotrode and other elements of the device, such that the liquefied sleeve material, under axial shortening of the anchoring sleeve, flows outward radially and penetrates the tissue surrounding the anchor.

The anchoring process can be controlled by, for example, the time for which the vibration source is switched on, or by the stroke of the anchor elements relative to one another, or the shortening of the anchoring sleeve respectively, and the anchoring process is ended by switching off the vibration source, possibly automatically. After re-solidification of the liquefied material, which only requires a very short time (at most a few seconds), the sonotrode and the sleeve system are separated from the now-anchored anchor (anchor foot and anchoring sleeve), and from the suture, and the sonotrode is de-coupled from the vibration source. The sonotrode and sleeve system are preferably disposable items; for the anchoring of another anchor a new device is coupled to the vibration source.

It is technically possible to realize the device (except for the most proximal portion) with an external diameter of the sleeve system of less than 8 mm and a sonotrode length in the range of about 10 to 20 cm, such that the device can be used with standard cannulas employed in arthroscopic surgery. The corresponding anchors have diameters from 2 to 6 mm, in particular 3 to 6 mm, and are designed to anchor from 1 to 4 sutures. Anchors for two sutures preferably have a diameter of about 4 mm and an axial length from 5 to 50 mm (preferably 10 to 20 mm for anchors with a diameter of 4 mm) and they comprise, for example, openings for two sutures (e.g. two eyelets). The tissue opening to be provided for the anchor has a diameter that is somewhat larger than the diameter of the anchor; preferably approximately 0.2 mm larger.

Circular cross-sections are preferred for the anchor and sleeve system for technical reasons having to do with manufacturing, but since the anchoring process involves essentially no rotational motion, non-circular cross-sections are possible also.

The material for the anchor foot and anchoring sleeve may be resorbable or non resorbable, depending on the application. The material for the anchoring sleeve is to be liquefiable through the application of mechanical vibration, for instance ultrasonic vibration, at least where surfaces thereof are contact faces between a vibrating element and a counter element held against the vibrating element. Such liquefiable materials are, in particular, materials with thermoplastic properties. Preferred materials for the anchoring sleeve are resorbable polymers based on lactic acid and/or glycolic acid, in particular PLLA, PCLA or PCLLA, particularly Poly-LDL-lactide (e.g. available from Boehringer under the brand name Resomer LR708) or Poly-DL-lactide (e.g. available from Boehringer under the brand name Resomer R208). The material of the anchor foot must have sufficient mechanical strength, at least in the area of the suture opening (eyelet) for retaining the suture. For this reason, the anchor foot is composed of, for example, a metal, a ceramic material or a suitably solid polymer, which may also be a thermoplastic. Preferably, the anchor foot is made of PEEK. If correspondingly dimensioned, it is also possible to make complete anchors (anchoring sleeve and anchor foot) of a resorbable polymer.

Further materials for the anchoring sleeve are, for example, non-resorbable polymers such as polyolefins (e.g. polyethylene), polyacrylates, polymethacrylates, polycarbonates, polyamides (especially polyamide 11 or polyamide 12), polyesters, polyurethanes, polysulfones, liquid crystal polymers (LCPs), polyacetals, halogenated polymers, in particular halogenated polyolefins, polyphenylene sulphones, polysulfones, poly(aryletherketone)s (e.g. polyetheretherketone (PEEK), available from Invibo under the brand name Victrex 450G or Peek Optima), polyethers or corresponding copolymers, mixed polymers or composite materials containing the aforementioned polymers, or resorbable polymers like polyhydroxyalkanoate (PHA), polycaprolactones (PCL), polysaccharides, polydioxanone (PD), polyanhydrides, polypeptides, trimethylcarbonate (TMC) or corresponding copolymers, mixed polymers or composite materials containing the aforementioned polymers. Exemplary composite materials contain at least one resorbable or non-resorbable polymer and calcium phosphate (e.g. hydroxyapatite) as a filler (filler content preferably between 10 and 50 percent by weight).

BRIEF DESCRIPTION OF THE DRAWINGS

By means of the following Figs. three exemplary embodiments of the device according to the invention and their functional principles are described in detail and further embodiments derived therefrom are mentioned. Therein:

FIGS. 1 and 2 are an elevation (FIG. 1) and an axial section (FIG. 2) of a first exemplary embodiment of the device according to the invention;

FIGS. 6 and 7 show a second exemplary embodiment of the device according to the invention;

FIGS. 8 and 9 show, in a larger scale, the anchor of the device according to FIGS. 6 and 7 (axial sections and distal top view);

FIG. 10 shows successive phases of the anchoring process carried out with the device according to FIGS. 6 to 9;

DETAILED DESCRIPTION OF THE INVENTION

Figure 3:
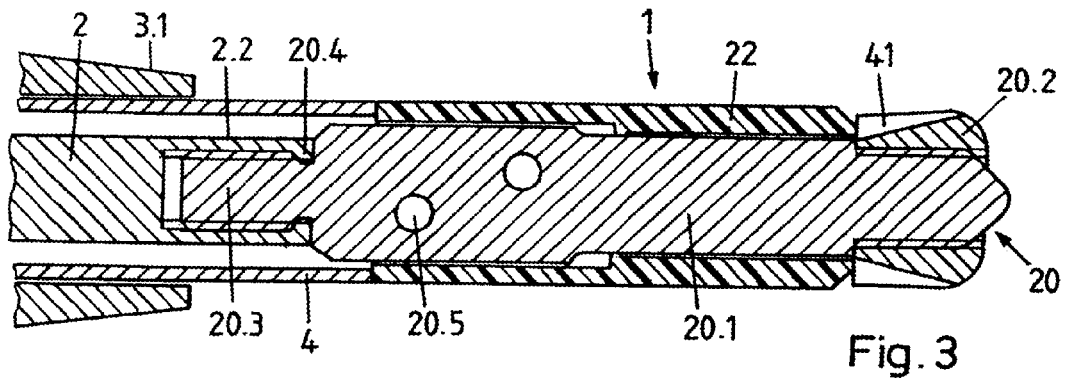
FIGS. 3 and 4 show, in a larger scale, the anchor of the device according to FIGS. 1 and 2 (two axial sections, the section planes being perpendicular to one another)
Figure 4:
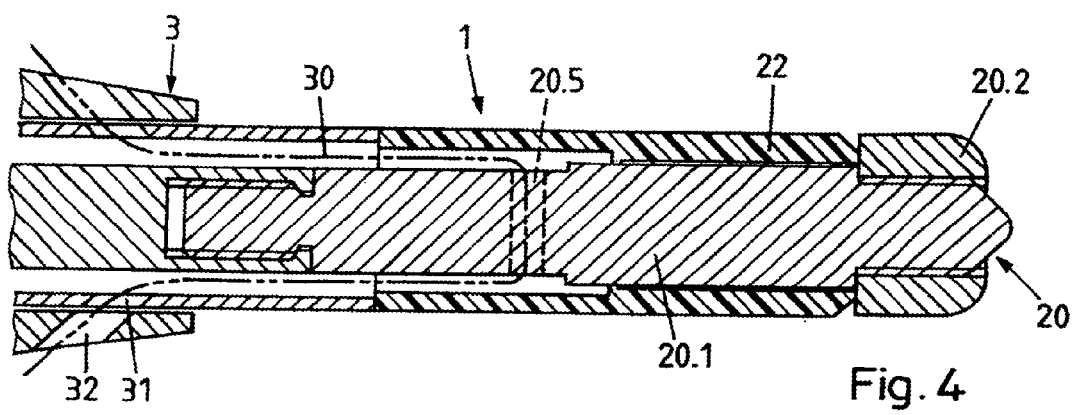

FIGS. 1 to 4 are an elevation (FIG. 1) and an axial section (FIG. 2) of a first exemplary embodiment of the device according to the invention, and further show, in a larger scale, an example of an anchor which is suitable for this embodiment (FIGS. 3 and 4, which are two axial sections, the two section planes being perpendicular to each other).

The device comprises a proximal end (left side in FIGS. 1 and 2) and a distal end (right side in FIGS. 1 and 2) opposite from the proximal end. Anchor 1 is arranged at the distal end of the device. A sonotrode 2 extends axially through a guide sleeve 3 from anchor 1 to the proximal end of the device. The proximal end 2.1 of the sonotrode is equipped for a coupling to the vibration source (not shown), for example by comprising a recessed socket with an internal thread at a proximal face (not shown), which is adapted to a corresponding threaded post situated on the vibration source. Radially, between guide sleeve 3 and sonotrode 2, extends a pushing mechanism, comprising a distal pushing sleeve 4, a pushing spring 5 adjacent to the proximal end of the pushing sleeve, an intermediate sleeve 6 adjacent to the proximal end of the pushing spring, and a tension spring 7 adjacent to the proximal end of the intermediate sleeve.

The guide sleeve 3 comprises a distal part 3.1 with a smaller diameter, for example approximately 8 mm or smaller, and a proximal part 3.2 with a larger diameter. The distal part 3.1 of the guide sleeve extends into the proximal part 3.2. In this overlapping area the two sleeve parts 3.1 and 3.2 are, for example, screwed together, in such a manner that within certain limits the guide sleeve 3 can be shortened by further screwing of the distal part into the proximal part and can be lengthened by corresponding unscrewing, whereby, as will be described below, the anchoring depth can be adjusted. However, the two guide sleeve parts 3.1 and 3.2 may also be connected in a fixed manner, wherein the aforementioned adjustability is then achieved with the aid of a spacing piece 34 which has an adjustable axial length, by e.g. being capable of being screwed into and out of the housing of the vibration source, and against which the guide sleeve rests during the anchoring process.

The proximal part 3.2 of the guide sleeve 3 is closed by a screw-on or snap-on stopper element 10, wherein the stopper element 10 comprises a through opening for the proximal sonotrode end 2.1. The proximal sonotrode end has a non-round cross-section, which corresponds to the cross-section of the through opening in the stopper element 10, in such a manner that the proximal sonotrode end 2.1 cannot turn in the through opening. The two cross-sections are for example equally sized and hexagonal. When positioned in the through opening of the stopper element 10, the sonotrode 2 turns together with the guide sleeve 3, which means that the sonotrode can be rotated by rotating the guide sleeve. If the sonotrode 2 is positioned more proximally relative to the guide sleeve 3, the proximal sonotrode end 2.1 protrudes fully from the stopper element 10, and therewith the sonotrode 2 is freely rotatable relative to the guide sleeve 3.

In the interior of the proximal guide sleeve part 3.2 the tension spring 7 is positioned, pre-stressed between the stopper element 10 and a head 6.1 of the intermediate sleeve 6, in such a manner that this head is pushed against an inner shoulder 3.3 of the proximal guide sleeve part 3.2. A tension release arm 11 extends radially through the head 6.1 of the intermediate sleeve 6 (or corresponding arm parts are integral parts of the head), and protrudes through bilateral, axially running, slit-shaped openings 12 on either side of the proximal guide sleeve part 3.2. These openings 12 comprise, at their proximal ends, an extension 12.1 which runs along the circumference of the guide sleeve part 3.2. The tension release arm 11 comprises an opening for the sonotrode 2, such that the sonotrode is freely moveable therethrough in an axial direction. The tension release arm 11 and the head 6.1 (and therewith the entire intermediate sleeve 6) are pressed against the distal end of the device by the spring force of the pre-stressed tension spring 7, such that the tension release arm is positioned at the distal ends of the openings 12. By moving the decompression arm 11 in a proximal direction and engaging it into the extensions 12.1 of the openings 12, the intermediate sleeve 6 is displaced proximally against the spring force of the tension spring 7, the tension spring 7 is tensioned and the pushing spring 5 is relieved such that the force transmitted by the pushing sleeve 4 to the anchoring sleeve 22 is relieved. In this configuration, it is possible to freely tune and test the vibration capabilities of the acoustic system of the vibration source and the device according to the invention, without thereby melting the anchoring sleeve. Moreover, by tensioning the tension spring 7, assembly of the anchor 1 is made easier.

FIGS. 3 and 4 show the anchor 1 and its connection to the sonotrode 2 and the pushing sleeve 4 in a larger scale, where once again the distal end of the device is shown on the right. The anchor 1 comprises an anchor foot 20 and an anchoring sleeve 22. The anchor foot 20 consists of, for example, a shank part 20.1 and a foot part 20.2, which is screwed into to the shank part. Therein, the foot part 20.2 has a diameter that essentially corresponds to the outer diameter of the pushing sleeve 4. The shank part 20.1 has a smaller diameter, such that the proximal end face of the foot part 20.2 being screwed to the shank part 20.1 constitutes a shoulder running around the shank part.

The distal end face of the anchoring sleeve 22 rests against the aforementioned shoulder. The anchoring sleeve 22 has a lumen, which is adapted to the shank part 20.1 of the anchor foot 20 such that the sleeve 22 sits loosely on the shank part. The proximal end of the shank part 20.1 advantageously protrudes somewhat beyond the anchoring sleeve 22 and exhibits a threaded pin 20.3 (or another appropriate means of connection) which is screwed into a corresponding threaded recess on the distal sonotrode end 2.2, thereby becoming part of the sonotrode 2 for the purposes of acoustic functionality. At the base of the threaded pin 20.3, a predetermined breaking point 20.4 is provided for being broken during separation of the sonotrode 2 from the anchored anchor 1 after the anchoring process, such that the threaded pin 20.3 and the sonotrode 2 can be separated from the anchored part of the anchor.

Intermediate sleeve 6, pushing spring 5, pushing sleeve 4 and anchoring sleeve 22 are adapted to one another and to the guide sleeve 3 such that when the tension release arm 11 is in its distal position the tension spring 7 tensions the pushing spring 5 via the intermediate sleeve 6, such that the pushing spring is capable of biasing the pushing sleeve 4 and therewith the anchoring sleeve 22 against the anchor foot 20, and to continue to do so while the anchoring sleeve is being shortened through the liquefaction of the sleeve material.

A middle area of the suture (or the sutures) 30, which is only shown in FIG. 4 (dashed and dotted line) runs through an eyelet 20.5, which is situated in the shank part 20.1 of the anchor foot 20. The two parts of the suture that protrude from either side of the eyelet 20.5, run between the shank part 20.1 of the anchor foot 20 and the anchoring sleeve 22 in a proximal direction through a suture opening 31 in the pushing sleeve 4 and a further suture opening 32 in the guide sleeve 3. From there the two parts of the suture 30 run in an axially-oriented suture groove 33 (FIG. 1) which is located on the outside of the guide sleeve, and the suture ends are wound up in a store groove 35 on the proximal part 3.2 of the guide sleeve, or in another appropriate suture magazine being part of the device. By means of the suture 30 the sonotrode 2 and the pushing mechanism are held in the guide sleeve 3, wherein the suture permits a limited axial movement of the sonotrode relative to the guide sleeve. To limit the sonotrode movement distally relative to the guide sleeve 3, a proximal portion of the sonotrode 2 may feature a cross section that is larger than that of the distal sonotrode portion (as shown in FIG. 2), such that this proximal sonotrode portion cannot be pushed into the lumen of the intermediate sleeve 6.

As can be seen in FIGS. 3 and 4, the shank part 20.1 of the anchor foot 20 has a flattened cross section in the vicinity of the eyelet 20.5, such that the space between the shank part 20.1 and the anchoring sleeve 22 is greater on the sides featuring the eyelet opening than on the sides where no eyelet opening is present. The suture 30 runs through this widened space (FIG. 4), and is thereby prevented from getting into contact with liquefied material of the anchoring sleeve 22 during the anchoring process, which means that its free movement through the eyelet 20.5 is maintained also when the anchoring is complete.

The sonotrode preferably is made of metal, for example of titanium. The guide sleeve 3 and the intermediate sleeve 6 are, for example, made of plexiglass. The pushing sleeve material is chosen such that during the anchoring process the pushing sleeve 4 sticks or bonds as little as possible to the anchoring sleeve 22. The pushing sleeve is, for example, made of titanium or, to increase the stiffness of the sleeve system, of chromium steel.

The sonotrode 2 is acoustically designed such that the foot part 20.2 of the anchor foot 20 being threaded into the sonotrode, vibrates with maximum longitudinal amplitude. This is achieved when the sonotrode 2 together with the anchor 1 have an overall length that corresponds to a half or a whole wavelength of the vibration provided by the vibration source, and if the vibration source is set up such that the coupling point is also a point of maximal longitudinal amplitude. For the device described above, a frequency of 30 kHz gives a sonotrode length of approximately 180 mm (a whole wavelength), which is very compatible with the use of the device together with a standard cannula employed in arthroscopic surgery.

The first embodiment of the device according to the invention, described by aid of FIGS. 1 to 4, represents a closed load frame, in that the pushing mechanism (elements 4, 5, 6 and 7) and the anchoring sleeve 22 are clamped between the guide sleeve 3 and the anchor foot 20, wherein, during the anchoring process, the guide sleeve 3 is braced against the tissue and the housing of the vibration source, and the anchor foot 20 is attached to the sonotrode, which in turn is attached in the housing of the vibration source. The shortening of the anchoring sleeve 22 that occurs during the anchoring process is compensated by the lengthening of the pushing spring 5.

The first embodiment of the device according to the invention has the following four configurations:

Rest configuration: the sonotrode 2 is secured from rotating against the guide sleeve 3 (proximal sonotrode end held in the stopper element 10), the tension release arm 11 is preferably in its proximal position (tension spring 7 compressed, pushing spring 5 substantially without tension, only light pressure on the anchor 1). The suture is stretched between anchor 1 and store groove 35 such that it lies in the suture groove 33. The device is stored, supplied, and coupled to the vibration source while in this rest configuration, wherein the force necessary for screwing it to the vibration source is applied to the guide sleeve 3.

Test configuration: The spacing piece 34 (FIG. 2) is placed between the proximal end of the guide sleeve 3 and the housing of the vibration source, for example screwed into the housing, and thus the sonotrode is pulled out of its rotation-locked position. The tension release arm 11 remains in its proximal position. In this configuration the device and its connection to the vibration source is tested and tuned by shortly activating the vibration source. The device operates correctly, if the power consumed by the vibration source is within a predetermined range. As there is no significant pressure on the anchoring sleeve in this configuration, no liquefaction of the sleeve material occurs.

Anchoring configuration: The tension release arm 11 is moved from its proximal position and, by the force of the tension spring 7 is brought to its distal position, whereby the pushing spring 5 is tensioned. In this configuration, the distal end of the device is positioned in an opening provided in the tissue, such that the distal end face of the guide sleeve 3 is brought into contact with the tissue surface and the guide sleeve abuts the spacing piece 34. If necessary, through adjustment of the spacing piece or by screwing the distal part 3.1 of the guide sleeve in or out of the proximal part 3.2 of the guide sleeve, the anchoring depth (distance between the distal end of the anchor 1 and the distal end face of the guide sleeve 3 and/or the tissue surface) is adjusted. If necessary, the suture is re-tightened. The anchoring process is initiated by switching the vibration source on.

Separation configuration: The suture is loosened from the guide sleeve 3. In this configuration the sonotrode 2 is separated from the anchor 1 by a light pull, whereby the predetermined breaking point on the shank part 20.1 of the anchor foot 20 is broken, so that the sonotrode 2 together with the guide sleeve 3 and the pushing mechanism can be removed from the anchored anchor.

Figure 5:
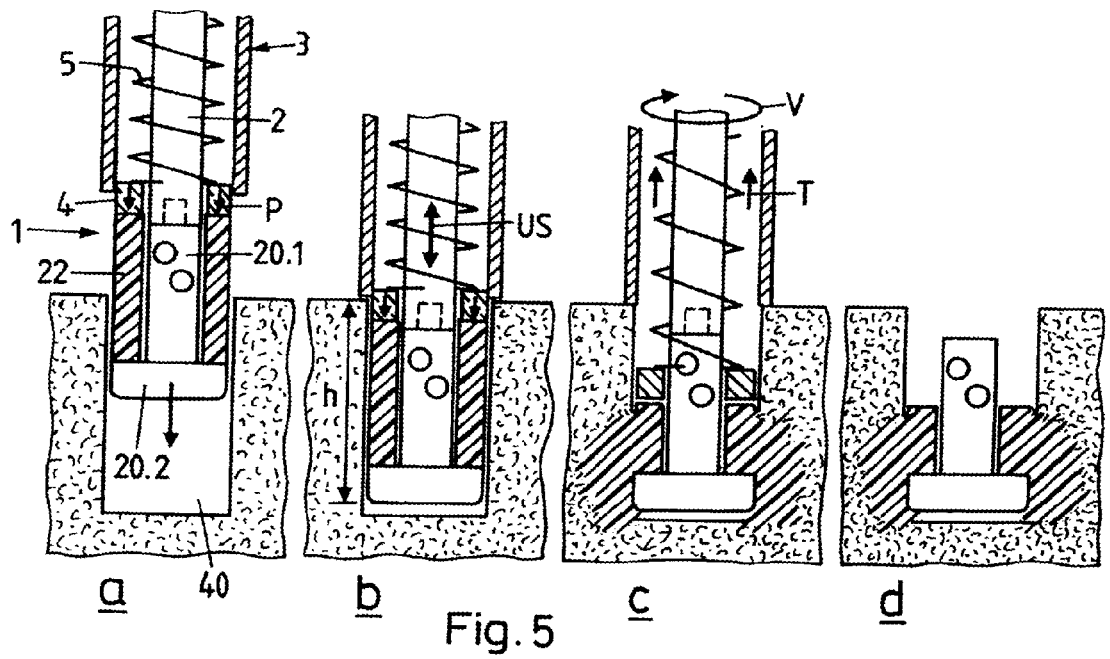
FIG. 5 shows successive phases of the anchoring process carried out with the device according to FIGS. 1 to 4.

FIG. 5 shows in a more diagrammatic way four successive phases (a to d) of an anchoring process carried out with the first embodiment of the device according to the invention. Only the anchor 1 and distal portions of sonotrode 2, guide sleeve 3 and pushing mechanism (pushing sleeve 4 and pushing spring 5) are shown.

In phase a, the anchor 1, which forms the distal end of the device according to the invention, is positioned in a suitably provided tissue opening 40, wherein the depth of the tissue opening 40 and the anchoring depth h are adapted to one another such that the foot part of the anchor foot does not rest against the bottom end of the opening. The device is in the anchoring configuration, this means that, through the force of the pushing spring 5, the pushing sleeve 4 is pressed against the anchoring sleeve 22 and the foot part 20.2 (arrow P).

In phase b, the anchor 1 is positioned (distal end face of the guide sleeve 3 sits against the tissue surface) and the vibration source is switched on (double arrow US). Through this action, in phase c, the material of the anchoring sleeve 22 liquefies and penetrates into the surrounding tissue. Once a predetermined anchoring time has elapsed or a predetermined shortening of the anchoring sleeve 22 is achieved, the vibration source is switched off. However, it is also possible for the surgeon to freely and in an ad-hoc manner choose the anchoring time or, by making use of appropriate markings on the sonotrode and (transparent) guide sleeve, the anchoring stroke and therewith the volume of liquefied material.

In phase c, the separation configuration is established, i.e. the sutures are separated from the guide sleeve and the sonotrode 2 and/or the vibration source is rotated (arrow V) to detach the threaded pin, and the vibration source together with sonotrode 2, guide sleeve 3 and pushing mechanism are removed (arrow T). In phase d, the anchor is shown anchored and separated from the remainder of the device.

It can be seen in FIG. 5 that the depth of the anchor in the tissue depends on the anchor positioning and is not altered during the anchoring process. This gives an advantage over conventional screwed-in or impacted-in anchors, whose holding force in the tissue is inseparably related to the depth of their implantation.

As shown in FIG. 5, the material of the anchoring sleeve 22 liquefies preferentially at the contact face between the anchor foot 20 and the anchoring sleeve 22 as a result of the vibrations that are transmitted from the sonotrode 2 to the anchor foot 20. Depending on the combination of materials and the design of the contact faces, a concurrent or exclusive liquefaction of material at the contact face between anchoring sleeve 22 and pushing sleeve 4 can also be achieved. It is generally true that only a small part of the vibration of the anchor foot 20 will be transmitted through the anchoring sleeve 22, and therefore in the case where both contact faces comprise the same materials and the same design, liquefaction will occur mainly at the contact face with anchor foot 20. To achieve additional liquefaction at the contact with the pushing sleeve 4, it is necessary to place a material with a relatively lower glass transition temperature in that area, and/or to reduce the surface area of the contact face between anchoring sleeve 22 and pushing sleeve 4, for instance by tapering the anchoring sleeve 22 or by providing the contact face with energy-directing elements in the form of protruding ridges or peaks. It has been found that a pattern of alternating, radial ribs and grooves are particularly well suited for this function of energy focusing.

It is also possible to design the anchoring sleeve 22 as a two-part or multi-part element, wherein through appropriate design of the contact faces within the anchoring sleeve 22, liquefaction of material can be achieved, for example, in the middle of the anchoring sleeve. As already described above, the anchoring sleeve can feature a non-round inner and/or outer cross section. It is also not necessary that all cross sections of this anchoring sleeve have the form of closed rings. The sleeve may comprise a slit or slits which extend over part of the axial length or the whole axial length.

Whereas a welding between the anchor foot and the anchoring sleeve may be desirable, a corresponding welding between the anchoring sleeve and the pushing sleeve is to be prevented if possible. Welding is usually achieved if both materials are polymers and their glass transition temperatures are not more than 50° C. apart. A welding is prevented if the material of anchor foot 20 and/or pushing sleeve 4 is not liquefiable under the conditions of the anchoring process (as is the case with metal or ceramic) and is not wetted by the liquefied material of the anchoring sleeve 22.

If the anchor foot 20 is not welded to the anchoring sleeve 22 during the anchoring process, it is advantageous to provide recesses in the shoulder of the anchor foot 20 or the foot part 20.2 respectively, into which recesses the liquefied material flows, such that after re-solidification of the liquefied material, the anchor foot 20 and therewith the suture eyelets 20.5 are secured in the anchoring sleeve and prevented from being drawn out. Such recesses are represented in FIG. 3 and designated with 41.

The first embodiment of the device according to the invention may be varied, for example, in that the through opening for the sonotrode in the stopper element 10 is comprised by a round safety part being fastened via a predetermined breaking line in the stopper element. The predetermined breaking line is designed such that when the sonotrode is screwed onto the vibration source, the safety part breaks as soon as the screw connection is tight.

FIGS. 6 to 9 illustrate a second exemplary embodiment of the device according to the invention, wherein FIG. 6 is an elevation of the entire device and FIG. 7 an axial section of the entire device, and wherein FIGS. 8 and 9 are larger scale axial sections through the anchor and a top view of the distal end of the anchor.

The device once again comprises an anchor 1 at the distal end of the device, a sonotrode 2, a guide sleeve 3 and a suture 30 (dashed and dotted line in FIG. 8), wherein the sonotrode 2 extends from the anchor 1 through the guide sleeve 3 to the proximal end thereof. The guide sleeve 3 has a distal part 3.1 with a smaller cross section and a proximal part 3.2 with a larger cross section, the two sleeve parts being firmly connected together, screwed into one another or produced as one piece. The anchor 1 again comprises an anchor foot 20 and an anchoring sleeve 22, wherein the anchoring sleeve 22 comprises or consists of the liquefiable material and is shortened during the anchoring process. As distinct from the first embodiment, the second embodiment of the device according to the invention has no pushing mechanism, such that it is possible to further reduce the cross section of the distal portion of the device. Further differences consist of the fact that the device is not a closed load frame, that for the shortening of the anchoring sleeve it is necessary to move the vibration source, and that the suture takes on a more active role in the anchoring process.

The sonotrode 2 is at least in its distal portion tube-shaped with cross sections being adapted to the cross sections of the anchoring sleeve 22, and in its proximal portion it is equipped for being coupled to the vibration source (not shown), for instance with an inner thread, wherein the coupling to the vibration source is designed such that it allows a small axial movement (anchoring stroke) of the sonotrode 2 relative to the guide sleeve 3, without the guide sleeve 3 striking against the housing of the vibration source.

The sonotrode 2 and the guide sleeve 3 are functionally connected by a connecting pin 50, which is positioned through a radial bore through the sonotrode and for which two opposite slit-shaped and axially extending pin openings 51 are provided in the guide sleeve 3. The axial length of the openings 51 is adjustable at least in the proximal portion with the aid of an adjustment ring 52 which is screwed on to the distal part of the guide sleeve 3.1. The anchoring depth (distance between tissue surface and the distal end of the anchor 1) is set via the positioning of this adjustment ring 52.

The distal end of the proximal guide sleeve part 3.2 comprises a suture tensioning device 54, which for example, comprises a suture tensioning ring 54.1, an intermediate ring 54.2 and a locking ring 54.3, wherein the suture tensioning ring 54.1 is screwed on to the distal part of the guide sleeve 3.1 and thus is axially displaceable, and wherein the locking ring, when pulled against the intermediate ring, is capable of holding in place the suture which runs around it and to keep it tensioned in a self-locking manner.

FIGS. 8 and 9 show that the foot part 20.2 of the anchor foot 20 comprises for each suture two axial suture bores 20.6 (four bores for two sutures are shown) and the shank part of the anchor foot 20 is tube-shaped and comprises a broadened distal portion. This distal portion of the shank part 20.1 forms the shoulder upon which the anchoring sleeve 22 sits. Furthermore, this distal portion of the shank part is adapted to the proximal portion of the foot part 20.2 such that the two parts snap into one another for being fastened to each other.

A middle portion of the suture 30, a part of which is represented in FIG. 8 as a dashed and dotted line, runs through two of the suture bores 20.6 in the foot part 20.2 of the anchor foot 20 and is thereby held in the anchor. The two parts of the suture that protrude proximally out of the suture bores 20.6 run through the shank part 20.1 of the anchor foot and into the distal portion of the sonotrode 2, from where they run through aligned suture openings 32 in the sonotrode 2 and the guide sleeve 3 to the outside of the guide sleeve. From there they run in suture grooves 33 through the adjustment ring 52 into the suture tensioning device 54, i.e. through the suture tensioning ring 54.1, through corresponding axial openings in the intermediate ring 54.2, around the locking ring 54.3 and back through the intermediate ring 54.2. By pulling on the suture ends, which protrude from the intermediate ring 54.2, the suture 30 is tensioned and the locking ring is pulled against the intermediate ring 54.2 whereby the suture is locked and the suture tension maintained in a self-locking manner. For further tightening the suture, the tension ring is screwed into a further distal position. The suture ends are stored in the store groove 35.

The tension of the suture 30, which in the second embodiment of the device according to the invention is a relevant parameter, is such that, without substantial elastic stretching, the suture is able to accommodate the force which is to be imparted to the anchoring sleeve for liquefaction of the anchoring sleeve material and for shortening of the anchoring sleeve.

The materials for the individual elements of the device according to FIGS. 6 to 9 correspond to the materials described above for the first embodiment.

The sonotrode 2 is acoustically designed such that its distal end oscillates with a maximal longitudinal amplitude. If the coupling point of the vibration source also oscillates with a maximal longitudinal amplitude, the sonotrode length is, for example, as long as a half or a whole wavelength of the oscillation produced by the vibration source in the sonotrode material. The connecting pin 50 is situated in a node, i.e. for a sonotrode with the overall length of a whole wavelength, e.g. at a distance of ¾ of one wavelength from the distal sonotrode end.

The second embodiment of the device according to the invention has three configurations:

Rest and test configuration: the suture is tensioned just sufficiently for keeping the anchor in position in the sonotrode and the connecting pin is in its most proximal position. The device is stored, supplied, and coupled to the vibration source while in this configuration, wherein the necessary torque for screwing the sonotrode to the vibration source is applied, for example, to the connecting pin 50. In this configuration the vibration source is briefly switched on for functional testing and tuning, wherein the sonotrode is pressed against the anchoring sleeve by the suture tension only, and this pressure is not sufficient to achieve liquefaction of the anchoring sleeve material. When the power consumption of the vibration source is in a predetermined range, the device is ready for use.

Anchoring configuration: Before or after the introduction of the distal end of the device into the tissue opening (guide sleeve 3 rests upon the tissue surface) the anchoring depth can be set by adjustment of the adjustment ring 52 and if necessary the suture is tensioned (to increase the stability of the anchor on the sonotrode) through turning of the suture tension ring 54.1. In this configuration the sonotrode is pressed towards the anchor 1, the vibration source is switched on and thereby the anchor is anchored.

Separation configuration: the suture tensioning mechanism is loosened by displacing the locking ring 54.3 towards the proximal end of the device. In this configuration the anchored anchor is separated from the other elements of the device, by simply moving away these elements.

FIG. 10 shows in the same manner as FIG. 5 four successive phases a to d of the anchoring process carried out with the help of the second embodiment of the device according to the invention.

In phase a, the distal end of the device or the anchor 1 respectively is positioned in the tissue opening. The final position of anchor 1 in the tissue is reached, when the distal end face of the guide sleeve 3 rests against the tissue surface, as is the case in phase b. Next the vibration source is switched on and the sonotrode 2 is pressed against the anchoring sleeve 22, whereby the material of the sleeve is liquefied to flow out radially and whereby the anchoring sleeve 22 becomes shorter. The sonotrode 2 being pressed further moves relative to the guide sleeve 3, which rests on the tissue surface, as shown in phase c. The anchor 1 being held by the suture 30 remains stationary. The stroke of sonotrode 2 may be limited by the proximal end of the guide sleeve 3 abutting against the housing of the vibration source or by the connecting pin 50 abutting against the distal end of the pin opening 51 towards which the pin moves during the anchoring process. For setting different anchoring strokes, a further adjustment ring (not shown) may be provided at this distal end, which ring, depending on its position, closes the pin opening more or less distally. Phase d shows the anchored anchor 1, from which the other parts of the device have been removed after release of the suture 30 from the tensioning device 54.

As already described above in connection with the first embodiment of the device according to the invention, same materials and same contact faces between anchoring sleeve 22 and sonotrode 2 and between anchoring sleeve 22 and anchor foot 20, result in the sleeve material being primarily liquefied at the contact face with the sonotrode 2. A primary liquefaction at the contact face with anchor foot 20, as shown in FIG. 10, will be achieved when, for example, the anchoring sleeve 22 has on this side a tapering face, as shown in FIG. 8. The same effect can be achieved by providing at the distal end or the anchoring sleeve 22 a material with a relatively low glass transition temperature, while providing at its proximal end a non-liquefiable material or a thermoplastic with a higher glass transition temperature.

The second embodiment of the device according to the invention may be varied, for example, in that the pressure exerted by the sonotrode 2 on the anchoring sleeve 22 and the anchoring stroke are not effected by an operator, but that the device forms a closed load frame in which the sonotrode 2 is tensioned against the anchoring sleeve 22 in a manner such, that the force necessary for the anchoring can be maintained over the entire stroke. As described for the first embodiment, this can be realized for the second embodiment with a pushing spring being arranged in a pre-stressed state between the proximal part 3.2 of the guide sleeve and the connecting pin 50 and pressing the connecting pin 50 against the distal end of the pin opening 51. In such an arrangement the suture would need to be strong enough for taking up the spring force and, for the test configuration the pushing spring would have to be deactivated in a suitable manner.

Figure 12:
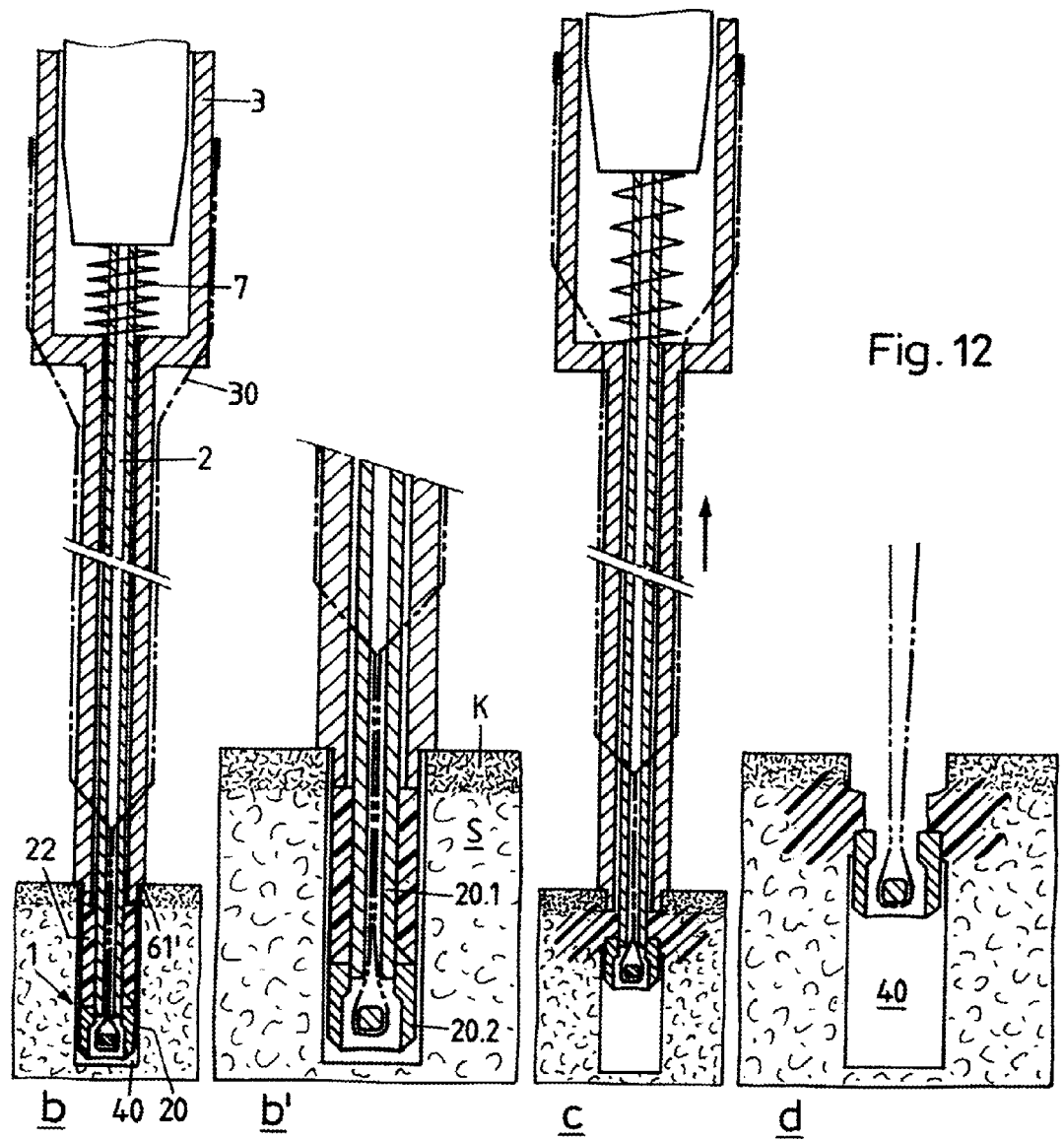
FIG. 12 shows successive phases of the anchoring process carried out with the device according to FIG. 11.

The anchoring process using the second embodiment of the device according to the invention may also be conducted as follows: During the anchoring process, the guide sleeve is braced against the housing of the vibration source, such that the vibration source and therewith the sonotrode cannot be moved against the tissue. The pressure necessary for the liquefaction of the anchoring sleeve material and for the anchoring stroke is effected by correspondingly pulling on the suture and moving the anchor foot towards the tissue surface. Such a procedure is particularly suitable for achieving an anchoring on the inner surface of the cortical bone, and therefore for an anchoring in a bone in which the cancellous tissue is absent or has a mechanical stability which is insufficient for the anchoring. In this case, the distance between the distal ends of the guide sleeve 3 and the sonotrode 2 is made to correspond to the thickness of the cortical bone. A similar anchoring, which is however achieved with the help of a different device, is shown in FIG. 12 and will be described in detail further below in connection with this FIG. 12.

Figure 11:
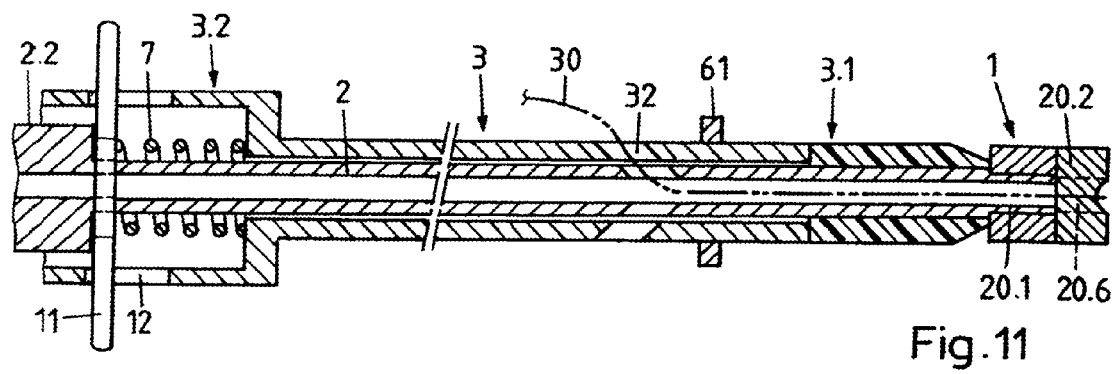
FIG. 11 is an axial section of a third exemplary embodiment of the device according to the invention.

FIG. 11 is an axial section of a third exemplary embodiment of the device according to the invention. This embodiment combines features of the first and second embodiments, in particular the feature of the closed load frame variant of the second embodiment, which is described above in addition to the variant illustrated in FIGS. 6 to 8, i.e. the variant in which a spring is provided for effecting the force and the stroke necessary for the anchoring process. As opposed to the described variant of the second embodiment, however, in the third embodiment the sonotrode effects the anchoring stroke by being moved away from the tissue during the anchoring process, and the anchor foot is firmly connected to the distal end of the sonotrode, as is the case for the first embodiment.

The third embodiment of the device according to the invention again comprises an anchor 1, a sonotrode 2, a guide sleeve 3 and a suture 30, wherein the guide sleeve takes on, in addition to the functions it performs in the first and second embodiments, the function of a stationary pushing device. The guide sleeve again comprises a distal part 3.1 with a smaller cross section and a proximal part 3.2 with a larger cross section. The distal part 3.1 comprises an axially movable (for instance with the help of matched screw threads, not shown) adjustment ring or a corresponding firm flange (or a step-shaped reduction in the cross section), the axial position of the adjustment ring 61 or the flange defining the anchoring depth (distance between the distal end of the anchor and the tissue surface).

The proximal end of the sonotrode 2 is again designed for a coupling to the vibration source and comprises a head 2.2 with a cross-section that is larger than the cross section of the remainder of the sonotrode 2. The sonotrode 2 is tube shaped, at least in a distal region, and is designed for the anchor foot 20 to be attached thereto, such that the anchor foot 20 becomes part of the acoustic system. This attachment must be capable of being separated for removal of the sonotrode 2 from the anchor foot 20 after the anchoring. This is achieved by, for example, outer threads of metal on the sonotrode side and inner threads of thermoplastic on the side of the anchor foot 20. Therein, the anchor foot 20 is designed such that during the anchoring process the region of its inner thread is warmed, so that at the end of the anchoring process the sonotrode 2 can be removed with a small tug that destroys the inner thread of the anchor foot 20. For the separation, it is also possible to provide a suitable predetermined breaking point on the side of the anchor foot 20, as described above with reference to the first embodiment of the device.

The sonotrode 2 is pressed against the guide sleeve 3 by a pre-loaded tension spring 7 being arranged between the sonotrode head 2.2 and an inner shoulder of the proximal guide sleeve part 3.2, and which presses the sonotrode head 2.2 in a proximal direction out of the guide sleeve. As in the first embodiment, the release of the sonotrode 2 from the spring force (test configuration), is achieved by a tension release arm 11 which is functionally connected to the tension spring 7, and through which the middle part of the sonotrode 2 passes in a manner to be independently movable. The movement of the tension release arm is guided in axially-extending openings 12 in the guide sleeve 3, which openings comprise a distal extension (not shown) perpendicular to the device axis. For release of the sonotrode, the tension release arm 11 is arrested in the distal extensions of the openings 12. If not so arrested, the tension release arm 11 is pressed against the sonotrode head 2.2 by the tension spring 7.

The anchor 1 again features an anchor foot 20, which in this embodiment may be one-piece or two-piece (with shank part 20.1 and foot part 20.2), and it comprises an anchoring sleeve 22 of the liquefiable material. The suture 30, which for example passes through two axial openings in the middle region of the foot part 20.2 of the anchor foot 20, runs through the shank part 20.1 into the tube-shaped sonotrode 2 and via another coordinated set of suture openings 32 in sonotrode 2 and guide sleeve 3 reaches the outside of guide sleeve 3, from where the suture ends run proximally into a suture magazine (not shown) which is integrated into the device. As the sutures run directly from the anchor foot 20 into the sonotrode, the sonotrode can take over the function of shielding the suture from liquefied material which in other embodiments is taken over by the shank portion 20.1 of the anchor foot, such that this shank portion 20.1 may be absent.

The device represents a closed load frame, within which the anchoring sleeve 22 is clamped between the anchor foot 20 and the distal end face of the guide sleeve 3 through the anchor foot 20 being fixed to the distal end of the sonotrode 2 and through the sonotrode 2 being tensioned against the guide sleeve by the action of the tension spring 7 in such a way that sufficient pressure acts on the anchoring sleeve 22 for liquefaction of the material of the anchoring sleeve 22 and for shortening of the anchoring sleeve is achieved under the influence of the vibrations provided by the vibration source. The named shortening is compensated by a lengthening of the tension spring and a corresponding stroke of the sonotrode. The sutures have no functional role in the anchoring process. This means that they may or may not be fastened to the guide sleeve.

The third embodiment of the device according to the invention may be varied by, for example, the omission of the tension spring 7, in which case the pressure and the anchoring stroke are effected by the operator who pulls on the vibration source or on the suture, as described above in connection with the second embodiment. Furthermore the third embodiment of the device according to the invention can be varied in that in place of the adjustment ring 61 or fixed flange a further sleeve is placed outside the guide sleeve, the further sleeve being axially displaceable relative to the guide sleeve.

FIG. 12 shows three successive phases of an anchoring process, wherein, in analogy to the denominations in FIGS. 5 and 10, the phases are designated with b, c and d and wherein phase b' is a larger representation of phase b. The anchoring is achieved with the help of a variant of the device according to FIG. 11. In phase b the distal end of the device, or the anchor 1 respectively, is positioned in a tissue opening 40, such that a step 61' (same function as that of the adjustment ring 61 in FIG. 11) of the distal region of the guide sleeve, rests on the tissue surface. The vibration source is switched on. As a result, the sonotrode 2, driven by the tension spring 7 and permitted by the liquefaction of the material of the anchoring sleeve 22, moves in a proximal direction, while the guide sleeve 3 remains stationary (phase c). The liquefied material flows into the surrounding tissue. For the separation of the anchor (phase d) the suture is simply loosened from the guide sleeve 3 and the sonotrode is separated from the anchor foot 22 and removed along with the guide sleeve 3.

As already explained above, the embodiment depicted in FIG. 12 is particularly suited for an anchoring on the inner surface of the cortical bone K (subcortical anchoring), which is particularly advantageous if the cancellous bone S is absent or has mechanical properties that are completely insufficient for an anchoring. As shown in FIG. 12, in such an application the distance between the step 61' and the distal end of the guide sleeve 3 corresponds to the thickness of the cortical bone and the anchoring sleeve 22 is relatively short. In the course of the anchoring process, during which the distal end of the anchoring sleeve 22 is melted, the anchoring sleeve is shortened and in a final phase approaches the inner surface of the cortical bone, where a significant portion of the anchoring is generated. The anchor foot 20 is composed of, for example PEEK or PLDLA, while the anchoring sleeve 22 is composed of PLDLA and is welded to the anchor foot during the anchoring process.

Figure 13:
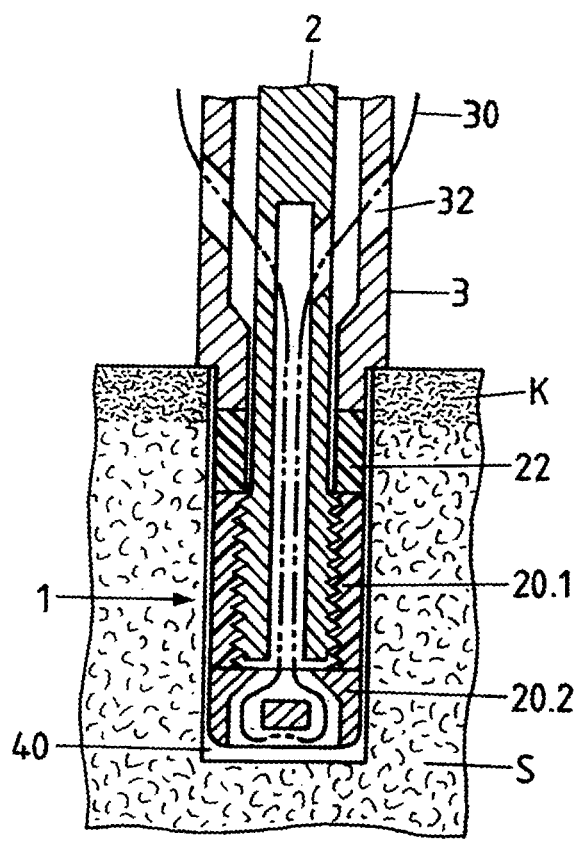
FIG. 13 shows a further exemplary embodiment of an anchor, which is suitable for the device according to FIG. 11 and a subcortical anchoring.

FIG. 13 depicts a further variant of an anchor 1, which is suitable for the device according to FIG. 11 and the method according to FIG. 12, and which is depicted as forming the distal end of the device according to the invention and positioned in a tissue opening 40. Elements with the same functionality are denominated with the same reference numbers as in the previous Figs.

The anchor 1 again comprises an anchor foot 20 and an anchoring sleeve 22, wherein the anchor foot 20 comprises a shank part 20.1 and a foot part 20.2. The shank part 20.1 has a substantially identical cross section as the anchoring sleeve 22, and its proximal end face is the shoulder against which the anchoring sleeve rests. The shank part 20.1 is, for example, attached to the distal end of the sonotrode by being screwed into an internal thread as shown. The foot part 20.2 is, for example, held in position by the suture 30 or it is screwed to the shank part. The foot part 20.2 and the shank part 20.1 are made of for example PEEK, while the anchoring sleeve is made of PLDLA. However it is also possible for all three anchor parts to be made of PLDLA. In each case the attachment of the shank part 20.1 to the sonotrode end is designed such that the sonotrode can be detached after the anchoring process (if necessary by destruction of attachment means). Preferably the materials of the anchor are chosen such that during the anchoring process the shank part 20.1 is welded together with the anchoring sleeve and possibly also with the foot part 20.2 which welding occurs for a material pairing of PEEK and PLDLA.

In the above paragraphs, three embodiments of the device according to the invention are described in a greater or lesser degree of detail, and a number of variants of these embodiments are mentioned. One skilled in the art is easily capable to suitably adapt characteristics of one embodiment to be applicable in other embodiments and/or to utilize in one embodiment, instead of characteristics which are described without detail or not at all for this embodiment, suitably adapted characteristics of other embodiments.

What is claimed is:

1. A device for the anchoring of a suture in bone tissue, which device comprises:
    a suture anchor, the suture anchor comprising an anchor foot with a proximally-facing shoulder;
    the suture which runs through the anchor foot;
    an anchoring sleeve with an axially extending through-going sleeve lumen open towards a distal side, the anchoring sleeve sitting against the shoulder, the anchoring sleeve comprising a solid liquefiable thermoplastic material;
    an insertion tool proximally of the anchoring sleeve; and
    a guide sleeve with a through-going axial lumen and a distal end open towards a distal side;
    wherein the insertion tool extends in the lumen of the guide sleeve and is capable of axial movement relative to the guide sleeve;
    wherein the suture at least in a distal guide sleeve region runs through the axial lumen of the guide sleeve;
    wherein the insertion tool is equipped for charging the anchoring sleeve with energy for liquefying portions of the solid thermoplastic material;
    and wherein the thermoplastic material of the anchoring sleeve is capable of being liquefied at least partially due to the energy impinging and is arranged for being forced to flow, in a liquefied state, out and penetrate surrounding bone tissue and thereby anchoring the anchor in the bone tissue.

2. The device according to claim 1, wherein the suture at least in an insertion tool region runs through an interior of the insertion tool.

3. The device according to claim 1, wherein the insertion tool is an energy transferring element capable of coupling energy into the anchoring sleeve for liquefying material of the anchoring sleeve.

4. The device according to claim 3, wherein the insertion tool is a sonotrode comprising a distal end and a proximal end, the proximal end being designed for coupling the sonotrode to a vibration source.

5. The device according to claim 4, wherein the anchoring sleeve is clamped or clampably arranged between the anchor foot and the sonotrode.

6. The device according to claim 1, wherein the anchoring sleeve is clamped or clampably arranged between the anchor foot and the guide sleeve.

7. The device according to claim 1, further comprising a pushing sleeve extending in the lumen of the guide sleeve, wherein the anchoring sleeve is clamped or clampably arranged between the anchor foot and the pushing sleeve.

8. The device according to claim 1, wherein a proximal portion of the anchor foot is mechanically firmly connected to the insertion tool.

9. The device according to claim 1, wherein the anchor foot comprises a shank part and a foot part, wherein the foot part is attached or attachable to the distal end of the shank part, and wherein the foot part forms the shoulder.

10. The device according to claim 9, wherein the shank part is substantially tubular, and wherein the suture runs through the shank part in an axial direction.

11. The device according to claim 1, wherein the guide sleeve comprises an opening proximally of a distal end thereof, and wherein the suture runs through said opening.

12. The device according to claim 11, wherein the suture at least in an insertion tool region runs through an interior of the insertion tool, and wherein the insertion tool comprises an insertion tool opening, and the suture runs through both, the insertion tool opening and the opening of the guide sleeve.

13. The device according to claim 12, wherein the insertion tool opening and the opening of the guide sleeve are aligned with each other.

14. A method for the anchoring of a suture in tissue, the method comprising the steps of:
providing a tissue opening having an opening cross-section and an opening depth,
providing a device comprising
a suture anchor, the suture anchor comprising an anchor foot with a proximally-facing shoulder;
an anchoring sleeve with an axially extending through-going sleeve lumen open towards a distal side, the anchoring sleeve sitting against the shoulder, the anchoring sleeve comprising a solid liquefiable thermoplastic material;
an insertion tool proximally of the anchoring sleeve; and
a guide sleeve with a through-going axial lumen and a distal end open towards a distal side, the insertion tool extending in an interior of the lumen;
using the insertion tool to couple energy into the anchoring sleeve to liquefy the material of the anchoring sleeve at least partially and forcing liquefied material of the anchoring sleeve to flow out and penetrate surrounding bone tissue, while the suture at least in a distal guide sleeve region runs through the axial lumen of the guide sleeve; and
causing the liquefied thermoplastic material to re-solidify to yield an anchoring of the anchor in the bone tissue.

15. The method according to claim 14, wherein the energy coupled in the anchoring sleeve is mechanical vibration energy, and wherein the mechanical vibration energy is coupled into the anchoring sleeve via the insertion tool directly or indirectly.

16. The method according to claim 14, wherein, during the anchoring process, the anchor is positioned stationary in the tissue opening, and wherein the anchoring sleeve is shortened resulting from the liquefaction.

17. The method according to claim 14, wherein, during the anchoring process, the anchor foot is moved toward a mouth of the tissue opening for compensating a shortening of the anchoring sleeve due to the liquefaction.

18. The method according to claim 14, wherein the tissue is bone tissue.

19. The method according to claim 18, wherein the bone tissue comprises a cortical outer layer with an interior limit, and wherein, for an anchoring of the anchor at the inner limit of the cortical outer later, the device is positioned in the tissue opening such that a proximal end of the anchoring sleeve is aligned with the inner limit of the cortical outer layer.

20. The method according to claim 14, wherein an anchoring depth is set such that the anchor foot is positioned below the tissue surface.

* * * * *